(12) United States Patent
Myers

(10) Patent No.: US 11,771,440 B1
(45) Date of Patent: Oct. 3, 2023

(54) BURRING DEVICES, SYSTEMS, AND METHODS

(71) Applicant: Kevin Ray Myers, Plano, TX (US)

(72) Inventor: Kevin Ray Myers, Plano, TX (US)

( * ) Notice: Subject to any disclaimer, the term of this patent is extended or adjusted under 35 U.S.C. 154(b) by 0 days.

(21) Appl. No.: 18/166,940

(22) Filed: Feb. 9, 2023

Related U.S. Application Data

(60) Provisional application No. 63/370,067, filed on Aug. 1, 2022.

(51) Int. Cl.
  *A61B 17/16* (2006.01)
  *A61B 34/00* (2016.01)

(52) U.S. Cl.
  CPC ...... *A61B 17/1626* (2013.01); *A61B 17/1617* (2013.01); *A61B 34/00* (2016.02)

(58) Field of Classification Search
  CPC . A61B 17/16; A61B 17/1613; A61B 17/1615; A61B 17/1617; A61B 17/162; A61B 17/1622; A61B 17/1624; A61B 17/1626; A61B 17/1628; A61B 17/32; A61B 17/3205; A61B 17/3207; A61B 17/320758; A61B 17/320766; A61B 2017/320766; A61B 2017/320775
  See application file for complete search history.

(56) References Cited

U.S. PATENT DOCUMENTS

| | | | |
|---|---|---|---|
| 4,923,462 A * | 5/1990 | Stevens | A61B 17/320758 606/159 |
| 5,409,493 A | 4/1995 | Greenberg | |
| 6,053,923 A * | 4/2000 | Veca | A61B 17/32002 606/80 |
| 6,511,493 B1 * | 1/2003 | Moutafis | A61B 17/320758 606/167 |
| 6,757,582 B2 | 6/2004 | Brisson et al. | |
| 7,077,845 B2 * | 7/2006 | Hacker | A61B 17/32002 606/180 |
| 7,465,309 B2 | 12/2008 | Walen | |

(Continued)

FOREIGN PATENT DOCUMENTS

| | | | | |
|---|---|---|---|---|
| AU | 2013215534 A1 * | 9/2014 | | A61B 17/1688 |
| CN | 111887929 B | 9/2021 | | |
| WO | WO 2021/178706 A1 | 9/2021 | | |

OTHER PUBLICATIONS

International Search Report and Written Opinion received in PCT Application No. PCT/US2023/069344 dated Aug. 3, 2023 in 9 pages.

*Primary Examiner* — Eric S Gibson
(74) *Attorney, Agent, or Firm* — Knobbe Martens Olson & Bear LLP

(57) ABSTRACT

A burring device for burring tissue, bone, or cartilage may include a shaft including a burr attached at a distal end. The shaft may be configured at a proximal end to be removably attached to a motor configured to drive a rotational movement of the burr. The device may include a housing configured to house the shaft in a lengthwise direction and at least a portion of the burr. The housing may be configured to allow rotational movement of the burr, and may include, at a distal portion, an opening through which at least a portion of the burr can extend beyond the housing. The shaft or the housing may be configured to be adjustably movable in a linear direction relative to each other so that at least a portion of the burr can extend beyond a distal end of the housing.

19 Claims, 6 Drawing Sheets

(56) References Cited

U.S. PATENT DOCUMENTS

| | | | |
|---|---|---|---|
| 8,062,319 B2 * | 11/2011 | O'Quinn | A61B 17/32002 606/180 |
| D679,811 S | 4/2013 | Hahn | |
| 8,491,585 B2 * | 7/2013 | Hannani | A61B 17/1671 606/80 |
| D694,406 S | 11/2013 | Hahn et al. | |
| 8,852,222 B2 | 10/2014 | O'Sullivan | |
| 8,894,654 B2 * | 11/2014 | Anderson | B23B 49/02 173/176 |
| 8,961,536 B2 | 2/2015 | Nikou et al. | |
| 9,381,022 B2 * | 7/2016 | Bradley | A61B 17/1615 |
| 9,855,106 B2 | 1/2018 | Jaramaz et al. | |
| 10,098,649 B2 | 10/2018 | Nikou et al. | |
| 10,105,152 B2 | 10/2018 | Nikou et al. | |
| 10,130,428 B2 | 11/2018 | Nikou et al. | |
| 10,188,406 B2 | 1/2019 | Matsuura et al. | |
| 10,350,008 B2 | 7/2019 | Gibbs et al. | |
| 10,695,074 B2 * | 6/2020 | Carusillo | A61B 90/06 |
| 10,813,574 B2 | 10/2020 | Fleig et al. | |
| 10,864,045 B2 | 12/2020 | Nikou et al. | |
| 11,051,830 B2 * | 7/2021 | Jaramaz | A61B 34/20 |
| 11,266,421 B2 | 3/2022 | Mitra et al. | |
| 2004/0181251 A1 * | 9/2004 | Hacker | A61B 17/32002 606/170 |
| 2006/0217751 A1 * | 9/2006 | O'Quinn | A61B 17/320783 606/180 |
| 2007/0060936 A1 * | 3/2007 | Benavitz | A61B 17/1633 606/180 |
| 2010/0286695 A1 * | 11/2010 | Hannani | A61B 17/1671 606/86 A |
| 2011/0245833 A1 * | 10/2011 | Anderson | B23B 49/02 606/80 |
| 2013/0197552 A1 * | 8/2013 | O'Brien, II | A61B 17/32002 606/1 |
| 2015/0366654 A1 | 12/2015 | Markarian | |
| 2019/0142453 A1 * | 5/2019 | Efremkin | A61B 17/320758 606/7 |

\* cited by examiner

BURRING DEVICES, SYSTEMS, AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

This disclosure generally relates to burring devices, systems, and methods for resecting a bone.

Description of the Related Art

Surgical instruments and methods for burring, for example during hip arthroscopy procedures, are well known in the art. Typically, surgical burring instruments are manually controlled, where a surgeon may burr a part of tissue, cartilage, or bone with a device, visually check an extent of burring, adjust the device, and then burr again as required. Such manual alignment(s)/adjustment(s) can be cumbersome, time-consuming, and inefficient. Furthermore, manual errors could also lead to over-burring or under-burring.

SUMMARY

There is a need for a burring device that is automated, accurate, and efficient. The embodiments disclosed herein each have several aspects, of which no single one is solely responsible for the disclosure's desirable attributes. Without limiting the scope of this disclosure, the prominent features are briefly discussed herein. After considering this discussion, and particularly after reading the section entitled "Detailed Description," one will understand how the features of the embodiments described herein provide advantages over existing tools relating to burring devices, systems, and methods.

The following disclosure describes non-limiting examples of some embodiments. For instance, other embodiments of the disclosed devices and methods may or may not include the features described herein. Moreover, disclosed advantages and benefits may apply only to certain embodiments of the invention and should not be used to limit the disclosure.

Burring devices, systems, and methods are described herein.

In one aspect of the disclosure, a burring device may be operable for burring tissue, bone, or cartilage. The device may include a shaft including a burr attached at a distal end thereof. The device may be configured at a proximal end thereof to be removably attached to a motor. The motor may be configured to drive a rotational movement of the burr.

The device may include a housing configured to house the shaft in a lengthwise direction. The housing may be configured to house at least a portion of the burr. The housing may be configured to allow rotational movement of the burr. The housing may include, at a distal portion thereof, an opening through which at least a portion of the burr can extend beyond the housing.

In some embodiments, the shaft may be configured to be adjustably movable in a linear direction relative to the housing. The shaft may be configured to be adjustably movable in a linear direction relative to the housing so that at least a portion of the burr can extend beyond a distal end of the housing by an extension amount.

In some embodiments, the housing may be configured to be adjustably movable in a linear direction relative to the shaft. The housing may be configured to be adjustably movable in a linear direction relative to the shaft so that at least a portion of the burr can extend beyond a distal end thereof by an extension amount.

In some embodiments, the burr may be removably attached to the shaft.

In some embodiments, the extension amount of the at least a portion of the burr beyond the distal end of the housing may be of a length in a range of 1 mm and 15 mm.

In some embodiments, the rotational movement of the burr may be in a range of 100 rotations per minute (rpm) and 10,000 rpm.

In some embodiments, the extension of the at least a portion of the burr beyond the distal end of the housing may be controlled by a computer-assisted surgical (CAS) system. The extension amount of the at least a portion of the burr beyond the distal end of the housing may be controlled by the CAS system in real-time. The real-time control of the CAS system may be based on real-time Magnetic Resonance Imaging (MRI) or Computer Tomography (CT) imaging of the tissue, bone, or cartilage anatomy.

In another aspect of the disclosure, a CAS system may burr tissue, bone, or cartilage. The system may include a burring device including a burr at a distal end of a shaft housed in a housing. The shaft and housing may be configured to be adjustably movable in a linear direction relative to each other. The shaft and housing may be configured to be adjustably movable in a linear direction relative to each other so that at least a portion of the burr can extend beyond a distal end of the housing.

In some embodiments, the CAS system may include at least one unit configured to measure or receive data related to anatomy of the tissue, bone, or cartilage.

In some embodiments, the CAS system may include at least one processor configured to calculate an amount of tissue, bone, or cartilage to be burred.

In some embodiments, the CAS system may include at least one processor configured to calculate an amount of extension of at least a portion of the burr beyond the distal end of the housing. The amount of extension may be based on the calculated amount of tissue, bone, or cartilage to be burred.

In some embodiments, the CAS system may include at least one unit configured to linearly adjust a position of the shaft and a position of the housing relative to each other. The at least one unit may linearly adjust a position of the shaft and a position of the housing relative to each other so that at least a portion of the burr extends beyond the distal end of the housing. The extension of the burr may be substantially equal to the amount of extension calculated by the at least one processor.

In some embodiments, the CAS system may include at least one unit configured to cause and/or adjust a rotational movement of the burr. The at least one unit may cause and/or adjust a rotational movement of the burr such that the burr may burr an amount of tissue, bone, or cartilage substantially equal to the calculated amount.

In some embodiments, the at least one unit configured to measure or receive data related to anatomy of the tissue, bone, or cartilage may be further configured to compare measured data to predetermined values.

In some embodiments, the measured or received data may include real-time data.

In some embodiments, the amount of tissue, bone, or cartilage to be burred may be calculated in real-time.

In some embodiments, the amount of extension of at least a portion of the burr beyond the distal end of the housing may be calculated in real-time.

In some embodiments, the position of the shaft and the position of the housing relative to each other may be linearly adjusted in real-time.

In some embodiments, the rotational movement of the burr may be caused and/or adjusted in real-time.

In some embodiments, the measured or received data may include MRI or CT imaging data of the tissue, bone, or cartilage.

In some embodiments, the calculation of the amount of tissue, bone, or cartilage to be burred may be based on a pre-determined value.

In some embodiments, the CAS system may include at least one memory unit configured to store data. The data may be related to the measured or received data, the calculation(s) of the amount(s) to be burred, the calculation(s) of the amount(s) of extension(s), position(s) of the burr relative to the distal end of the housing, and/or the rotational movement(s) of the burr.

In another aspect of the disclosure, a method for burring tissue, bone, or cartilage may include measuring or receiving data related to anatomy of the tissue, bone, or cartilage. The method may include calculating an amount of tissue, bone, or cartilage to be burred. The method may include calculating an amount of extension of at least a portion of a burr of a burring device beyond a distal end of a housing. The housing may house a shaft of the burr and at least a portion of the burr. The method may include linearly adjusting a position of the shaft and a position of the housing relative to each other. The position of the shaft and the position of the housing relative to each other may be linearly adjusted so that at least a portion of the burr extends beyond the distal end of the housing. The extension of the burr may be substantially equal to the calculated amount of extension. The method may include causing and/or adjusting a rotational movement of the burr. The rotational movement of the burr may be caused and/or adjusted such that the burr may burr the calculated amount of tissue, bone, or cartilage.

In some embodiments, the at least a portion of the burr may extend beyond the distal end of the housing in a range of 1 mm and 15 mm.

In some embodiments, the data related to anatomy may be measured or received in real-time.

In some embodiments, the amount of tissue, bone, or cartilage to be burred may be calculated in real-time.

In some embodiments, the amount of extension of at least a portion of the burr beyond the distal end of the housing may be calculated in real-time.

In some embodiments, the position of the shaft and the position of the housing relative to each other may be linearly adjusted in real-time.

In some embodiments, the rotational movement of the burr may be caused and/or adjusted in real-time.

In some embodiments, the measured or received data may include real-time MRI or CT imaging data of the tissue, bone, or cartilage.

In some embodiments, the calculation of the amount of tissue, bone, or cartilage to be burred may be based on a pre-determined value.

In some embodiments, the method may include storing data. The data may be related to the measured or received data, the calculation(s) of the amount(s) to be burred, the calculation(s) of the amount(s) of extension(s), position(s) of the burr relative to the distal end of the housing, and/or the rotational movement(s) of the burr.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawings, may be arranged, substituted, combined, and designed in a wide variety of different configurations, all of which are explicitly contemplated and made part of this disclosure.

DETAILED DESCRIPTION

The following detailed description is directed to certain specific embodiments of burring devices, systems, and methods. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. The embodiments of the invention, examples of which are illustrated in the accompanying drawings, are set forth in detail below. Wherever possible, the same reference numbers are used throughout the drawings to refer to the same or like parts.

Described herein are burring devices, systems, and methods. The burring devices, systems, and methods may be used in any surgical procedure requiring the removal or resection of bone, cartilage, enamel or other hard components of or on the human anatomy (e.g., orthopedic surgery, dental surgery etc.). For example, the burring devices disclosed herein may be used to perform a femoroplasty during hip arthroscopy. However, the burring devices, systems and methods described herein can be used in surgical procedures in other joints, or for other types of surgeries.

Figure 1:
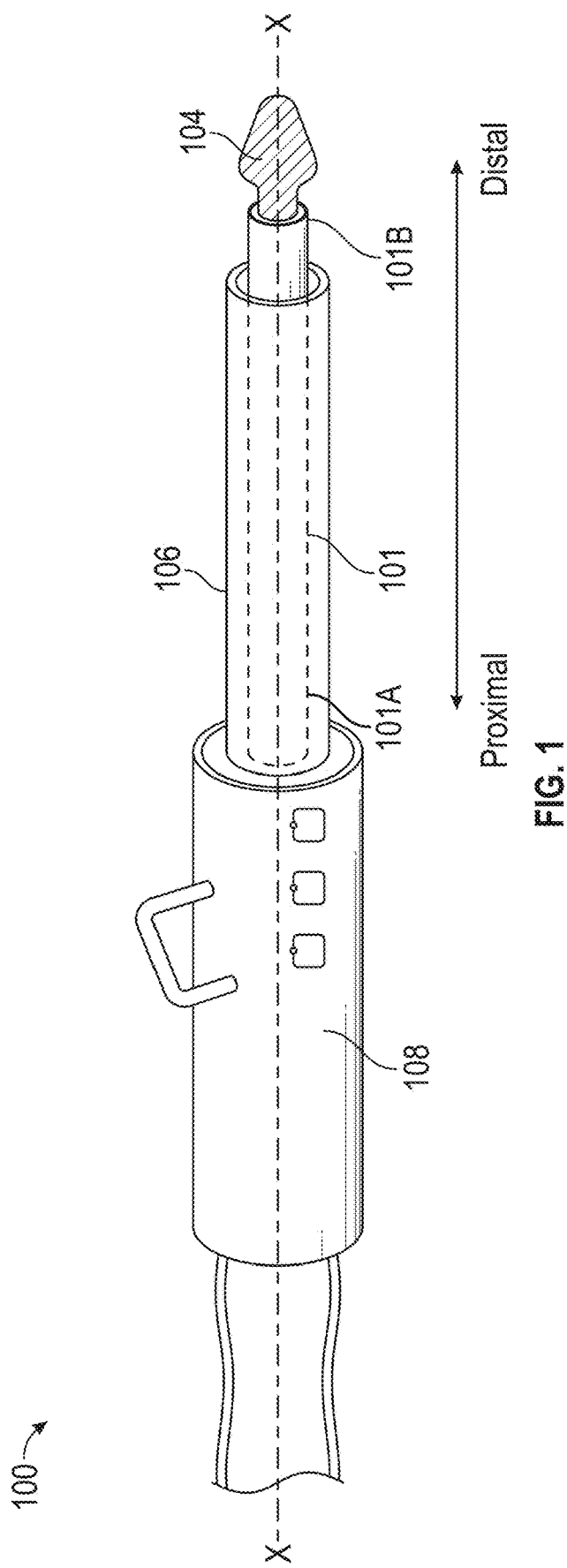
FIG. 1 is a schematic side view of an example burring device for burring tissue, bone, or cartilage.
Figure 6:
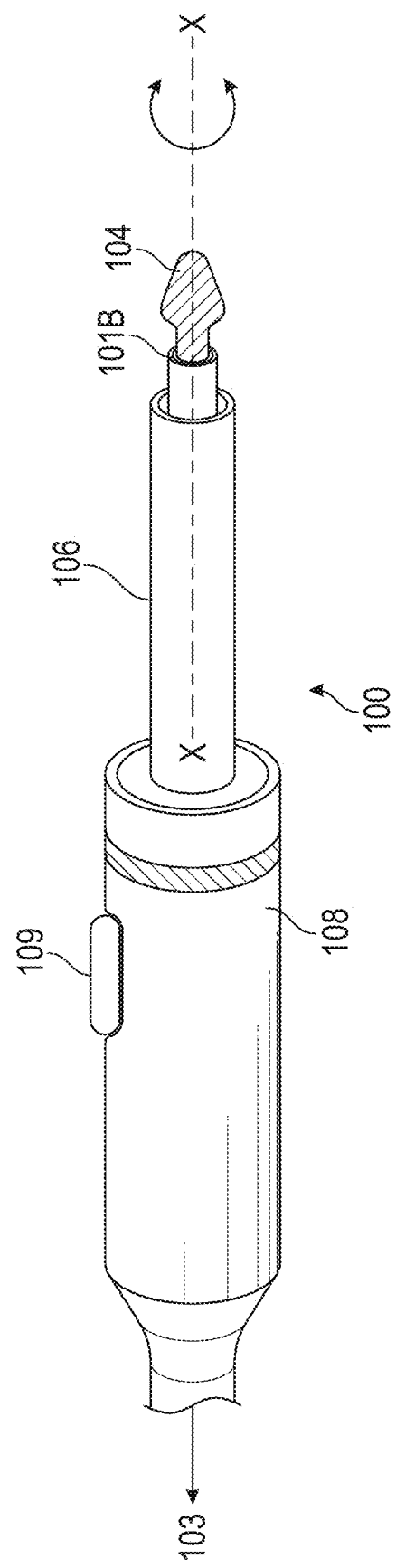
FIG. 6 is a schematic side view of an example burring device for burring tissue, bone, or cartilage, according to various embodiments.

FIGS. 1 and 6 show schematic side views of example burring devices for burring tissue, bone, or cartilage, according to various embodiments. Unless otherwise noted, components and functionality of the embodiments of FIGS. 1 and 6 may be the same or generally similar in other aspects of the disclosure.

Figure 2:
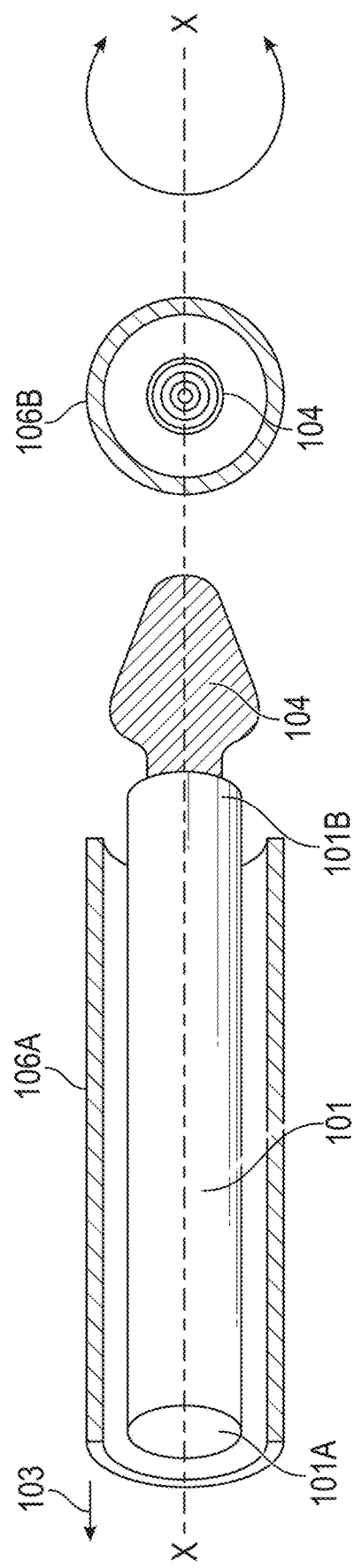
FIGS. 2A and 2B are enlarged schematic cross-sectional side and front views, respectively, of the shaft, housing, and burr of the burring device of FIG. 1.

In one aspect of the disclosure, a burring device 100 may be operable to burr tissue, bone, or cartilage (not shown). In some embodiments, the burring device 100 may include a shaft 101. The shaft 101 may have a proximal end 101A and a distal end 101B as shown in FIG. 2A.

In some embodiments, the burring device 100 may include a holding member or handle 108. In some embodiments, the shaft 101 may be attached at its proximal end 101A to the handle 108. The handle 108 may be adapted to be grasped by a hand of an operator. The handle 108 as depicted in FIG. 1 is merely for convenience and it is understood that any suitable handle may be substituted for the handle 108 as disclosed herein. In some embodiments, the handle 102 may be an ergonomic handle.

In some embodiments, the handle 108 may be adapted to be attached to different embodiments (e.g., different sizes and/or shapes of) of the shaft 101 and/or the housing 106. In some embodiments, the handle 108 may be adapted to be attached to the shaft 101 and/or the housing 106 such that at least a portion of the shaft 101 may slide into the handle 108 relative to the housing 106. In some embodiments, the handle 108 may be adapted to be attached to the shaft 101 and/or the housing 106 such that at least a portion of the housing 106 may slide into the handle 108 relative to the shaft 101. The handle 108 as depicted in FIG. 6 is merely for convenience and it is understood that any suitable handle may be substituted for the handle 108 as disclosed herein. In the illustrated embodiment, the handle 108 is co-linear (e.g., extends along the same axis) with the housing 106 and shaft 101. In some embodiments, the handle 108 may be parallel to an axis of the shaft 101 and/or a housing 106. In some embodiments, the handle 108 may be at an angle to an axis of the shaft 101 and/or the housing 106. In some embodiments, the handle 108 may be an ergonomic handle. In some embodiments, at least one control button 109 may be located at a surface of the handle 108 (see FIG. 6, for example). In some embodiments, the at least one control button 109 may start, stop and/or control a rotational movement of a burr 104 (e.g., operate the burr 104 to rotate in a clockwise or a counterclockwise direction). In some embodiments, the at least one control button 109 may start, stop and/or control a linear movement of the shaft 101 and/or a burr 104 relative to a housing 106 (e.g., by linearly moving the shaft 101 relative to the handle 108 while the housing 106 may be linearly fixed and/or by linearly moving the housing 106 relative to the handle 108 while the shaft 101 may be linearly fixed).

In some embodiments, the proximal end 101A of the shaft 101 may be removably attached to a motor 103 (not shown). In some embodiments, the proximal end 101a of the shaft 101 may be permanently attached to the motor 103 as show in FIG. 6. In some embodiments, the proximal end 101A of the shaft 101 may be removably attached to the handle 108. In some embodiments, the proximal end 101A of the shaft 101 may be permanently attached to the handle 108. The shaft 101 may be attached to the motor 103 at its proximal end 101A directly or indirectly via any suitable coupling mechanism (not shown). In some embodiments, the shaft 101 may be attached to the motor 103 at its proximal end 101A via the handle or the handle 108.

In some embodiments, the shaft 101 may be attached to a motor via a cord 105 as depicted in FIG. 1, where the shaft 101 and the handle 108 may be substantially axially aligned. In some embodiments, the shaft 101 may be attached to the motor 103 as depicted in FIG. 6, where the shaft 101 may be substantially aligned with an upper surface of the handle 108. In some embodiments, the shaft 101 may be angled respective to the handle 108. In some embodiments, the shaft 101 may be angled downward, upward, to the left, or to the right with respect to the upper surface to any exemplary non-limiting angle, for example, 45°, 90°, or 120°. In some embodiments, the shaft 101 may be curved in at least a section thereof at a proximal end 101A, distal end 101B, and/or any point therebetween. The curve may be directed to the right, left, upward, or downward. The shaft 101 may be rigid or flexible.

The shaft 101 may be made of any relevant material, including but not limited to steel, stainless steel, and/or any combination thereof.

In some embodiments, the motor 103 may drive a rotational movement of the shaft 101. In some embodiments, the rotational movement of the shaft 101 may be along a longitudinal axis X-X along a length of the shaft 101, as depicted in FIG. 1. It is understood that the motor 103 may be any suitable motor capable of driving a rotational movement of the shaft 101. The rotational movement of the shaft 101 may be clockwise, counterclockwise, or a combination thereof. The rotational movement of the shaft 101 may be in a range of 100 rpm and 10,000 rpm.

The distal end 101B of the shaft may be attached to a burr 104. In some embodiments, the burr 104 may be attached to the distal end 10Bb of the shaft 101 directly or indirectly via any suitable coupling mechanism (not shown). In some embodiments, the burr 104 may be removably attached to the shaft 101, allowing the burr 104 to be replaced or swapped (e.g., with a differently shaped burr). In other embodiments, the burr 104 may be permanently attached to the shaft 101.

In some embodiments, the burr 104 may be attached to the shaft 101 as depicted in FIG. 1, where the burr 104 may be substantially aligned with a length of the shaft 101. In some embodiments, the burr 104 may be angled respective to the shaft 101. In some embodiments, the burr 104 may be angled downward, upward, to the left, or to the right with respect to the shaft 101 to any exemplary non-limiting angle, for example, 45°, 90°, or 120°.

The burr 104 may be made of any material capable of burring tissue, bone, or cartilage, including but not limited to steel, stainless steel, tungsten carbide, diamond grit, and/or any combination thereof. In some embodiments, the material and/or shape of the burr 104 may allow it to burr through one material (e.g., bone, cartilage), but not other material (e.g., tissue).

The burr 104 may be of any suitable shape that may be used in burring tissue, bone, or cartilage, including but not limited to ball-shape, spear-shape, conical or frustoconical-shape, double-cone-shape, flame-shape, upside-down-cone-shape, football-shape, veneer-shape, pear-shape, cylinder-shape, wheel-shape, torpedo-shape, and/or any combination thereof.

In some embodiments, the burr 104 may have on at least a portion of a surface thereof features relevant to efficient and accurate burring of tissue, bone, or cartilage, including but not limited to, flutes to prevent unnecessary vibration(s), fine roughness, medium roughness, coarse roughness, and/or any combination thereof.

The motor 103 may drive a rotational movement of the burr 104. In some embodiments, the rotational movement of the burr 104 may be about a longitudinal axis X-X along a length of the shaft 101, as depicted in FIG. 1. In other embodiments, the rotational movement of the burr 104 may be at an angle to the longitudinal axis X-X. It is understood that the motor 103 (not shown) may be any suitable motor capable of driving a rotational movement of the burr 104. The rotational movement of the burr 104 may be clockwise, counterclockwise, or a combination thereof. The rotational movement of the burr 104 may be in a range of 100 rpm and 10,000 rpm.

The rotational movement of the shaft 101 may be identical to the rotational movement of the burr 104. In some embodiments, the rotational movement of the shaft 101 may be different from the rotational movement of the burr 104.

The burring device 100 may include a housing 106. FIGS. 2A and 2B show enlarged schematic cross-sectional side and front views, respectively, of the shaft 101, housing 106, and burr 104 of the burring device 100 according to various embodiments. The housing 106 may house at least a portion of the shaft 101 in a lengthwise direction as depicted in FIG. 2A. The housing 106 may allow rotational movement of the shaft 101 and/or the burr 104. In some embodiments, the rotational movement of the shaft 101 and/or the burr 104 may be about a longitudinal axis X-X along a length of the shaft 101, as depicted in FIGS. 2A and 2B.

In some embodiments, the housing 106 may house at least a portion of the burr 104. The housing 106 may include, at a distal portion thereof, an opening 106B through which at least a portion of the burr 104 can extend relative to (e.g., beyond) the housing (not shown). In some embodiments, the distal end 106B of the housing 106 may have a shape, including but not limited to tapered, rounded, conical, cylindrical, and/or a combination thereof, that may aid in the appropriate extension of the burr 104 relative to (e.g., beyond) the housing 106.

Figure 3:
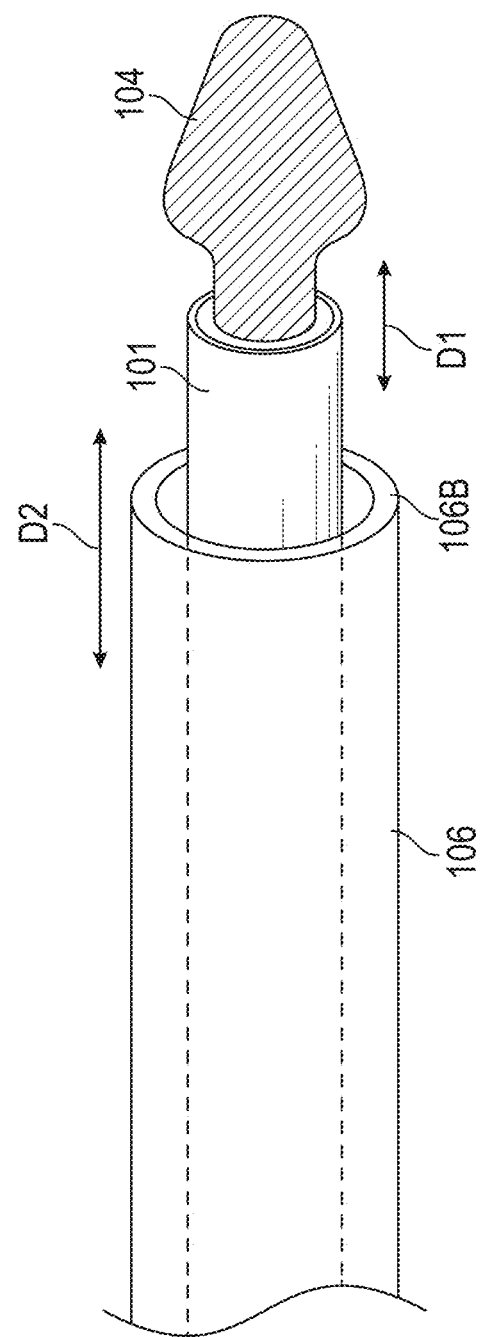
FIG. 3 is an enlarged schematic side view of the shaft, housing, and burr of the burring device of FIG. 1, showing a direction of movement of the shaft and/or burr relative to the housing, and a direction of movement of the housing relative to the shaft and/or burr.

In some embodiments, the shaft 101 may be adjustably movable in a linear direction relative to the housing 106. FIG. 3 shows an enlarged schematic side view of the shaft 101, housing 106, and burr 104 of the burring device 100 according to various embodiments. FIG. 3 also shows a direction of movement ("d1") of the shaft 101 and/or burr 104 relative to the housing 106 according to various embodiments. The shaft 101 may be adjustably movable in a linear direction relative to the housing 106 so that at least a portion of the burr 104 can extend relative to (e.g., beyond) the distal end 106B of the housing 106. See, for example, FIGS. 4B and/or 4C.

Unless otherwise noted, components and functionality of the embodiments of FIGS. 1, 2A, 2B and 3 may be the same or generally similar in other aspects of the disclosure.

In another aspect of the disclosure, the housing 106 may be adjustably movable in a linear direction relative to the shaft 101 (e.g., in addition to or in place of the shaft 101 being linearly movable relative to the housing 106). FIG. 3 shows a direction of movement ("d2") of the housing 106 relative to the shaft 101 and/or burr 104 according to various embodiments. The housing 106 may be adjustably movable in a linear direction relative to the shaft 101 so that at least a portion of the burr 104 can extend beyond the distal end 106B of the housing 106. See, for example, FIGS. 4B and/or 4C. In some embodiments, a position of the shaft 101 and/or a position of the burr 104 may be fixed (relative to the handle 108) and the housing 106 may move linearly (relative to the handle 108) to vary an amount that the shaft 101 and/or burr 104 extends relative to (e.g., beyond) the distal end 106B of the housing 106. In other embodiments, a position of the housing 106 may be fixed (relative to the handle 108), and the shaft 101 may move linearly (relative to the handle 108) to vary an amount that the shaft 101 and/or burr 104 extends relative to (e.g., beyond) the distal end 106B of the housing 106. In still other embodiments, both the housing 106 and the shaft 101 may move linearly relative to the handle 108 to vary an amount that the shaft 101 and/or burr 104 extends relative to (e.g., beyond) the distal end 106B of the housing 106.

Figure 4A:
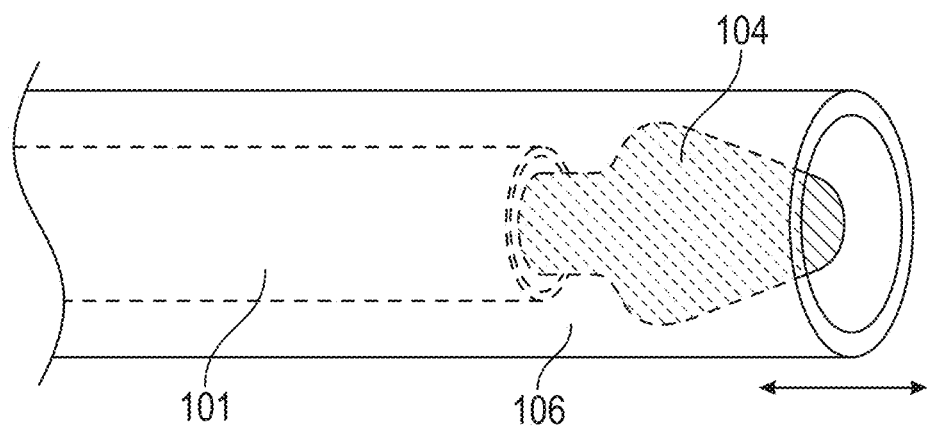
FIGS. 4A-4C are enlarged schematic side views of the shaft, housing, and burr of the burring device of FIG. 1, showing different positions of the shaft and/or burr relative to the housing.
Figure 4B:
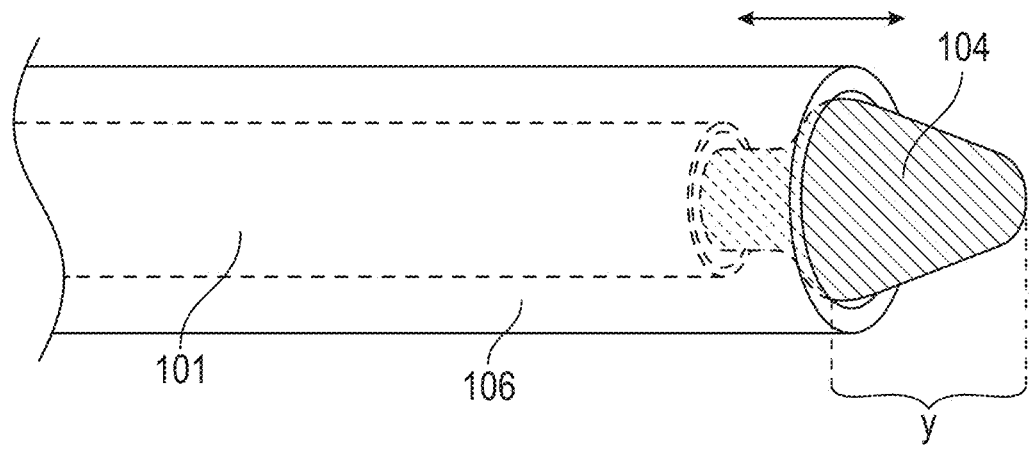
Figure 4C:
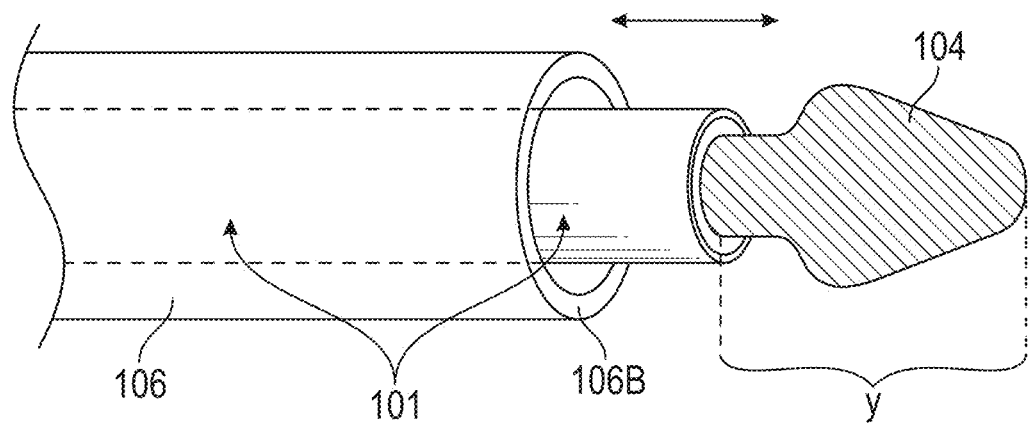

FIGS. 4A-4C show enlarged schematic side views of the shaft 101, housing 106, and burr 104 of the burring device 100 according to various embodiments. FIG. 4A shows, for example, a position of the shaft 101 and/or burr 104 relative to the housing 106 according to various embodiments, where no portion of the burr 104 extends beyond the distal end 106B of the housing 106. FIG. 4B shows, for example, a position of the shaft 101 and/or burr 104 relative to the housing 106 according to various embodiments, where at least a portion of the burr 104 extends beyond the distal end 106B of the housing 106 by a first amount. FIG. 4C shows, for example, a position of the shaft 101 and/or burr 104 relative to the housing 106 according to various embodiments, where the burr 104 and/or at least a portion of the shaft 101 extends beyond the distal end 106B of the housing 106 by a second amount greater than the first amount in FIG. 4B.

In some embodiments, the burr 104 may be removably attached to the proximal end 101A of the shaft 101. In some embodiments, the burr 104 may be attached to the shaft 101 via any coupling mechanism (not shown) that may allow attachment and/or removal of the burr 104 to/from the shaft 101.

In some embodiments, an extension "y" of at least a portion of the burr 104 beyond the distal end 106b of the housing 106 may be in a range of 1 mm and 15 mm. See, for example, FIG. 4B showing y. In some embodiments, the extension y of at least a portion of the burr 104 beyond the distal end 106B of the housing may include an entire length of the burr 104.

In some embodiments, a control mechanism (not shown) may control a linear movement of the shaft 101 and/or the burr 104 relative to the housing 106. The control mechanism (not shown) may include any mechanism that causes linear movement of the shaft 101 and/or the burr 104 relative to the housing 106 (e.g., by linearly moving the shaft 101 relative to the handle 108 while the housing 106 may be linearly fixed and/or by linearly moving the housing 106 relative to the handle 108 while the shaft 101 may be linearly fixed).

Such mechanisms may include, but are not limited to, click wheels, levers, springs, and/or a combination thereof. In some embodiments, the control mechanism (not shown) may be controlled by a computer-assisted surgical (CAS) system (not shown). In some embodiments, the control mechanism (not shown) may be controlled by the CAS system (not shown) in real-time. In some embodiments, the control mechanism (not shown) may be in proximity to the handle 108. In some embodiments, the control mechanism (not shown) may be at a location to allow a user to use the control mechanism by a same hand holding the handle 108.

In some embodiments, a locking mechanism (not shown) may lock or unlock a position of the shaft 101 and/or the burr 104 relative to the housing 106 in a position desired by a user. In some embodiments, the locking mechanism (not shown) may be a part of the control mechanism (not shown) controlling the linear movement of the shaft 101 and/or the burr 104 relative to the housing 106.

In some embodiments, the rotational movement of the shaft 101 and/or burr 104 may vary in a range between 100 rpm and 10,000 rpm. In some embodiments, the rotational movement of the shaft 101 and/or burr 104 may be set at a value within a range of 100 rpm and 10,000 rpm.

In some embodiments, extension of at least a portion of the burr 104 beyond the distal end 106B of the housing 106 may be controlled by the CAS system (not shown). In some embodiments, the extension of at least a portion of the burr 104 beyond the distal end 106B of the housing 106 may be controlled by the CAS system in real-time.

In some embodiments, the real-time control of the CAS system may be based on real-time Magnetic Resonance Imaging (MRI) or Computer Tomography (CT) imaging of the tissue, bone, or cartilage anatomy.

In some embodiments, the burring device 100 may measure pressure between at least a portion of a surface of the burr 104 and at least a portion of a surface of the tissue, bone, or cartilage to be burred. In some embodiments, the real-time control of the CAS system may be based on real-time pressure measurement between at least a portion of a surface of the burr 104 and at least a portion of a surface of the tissue, bone, or cartilage to be burred.

Figure 5:
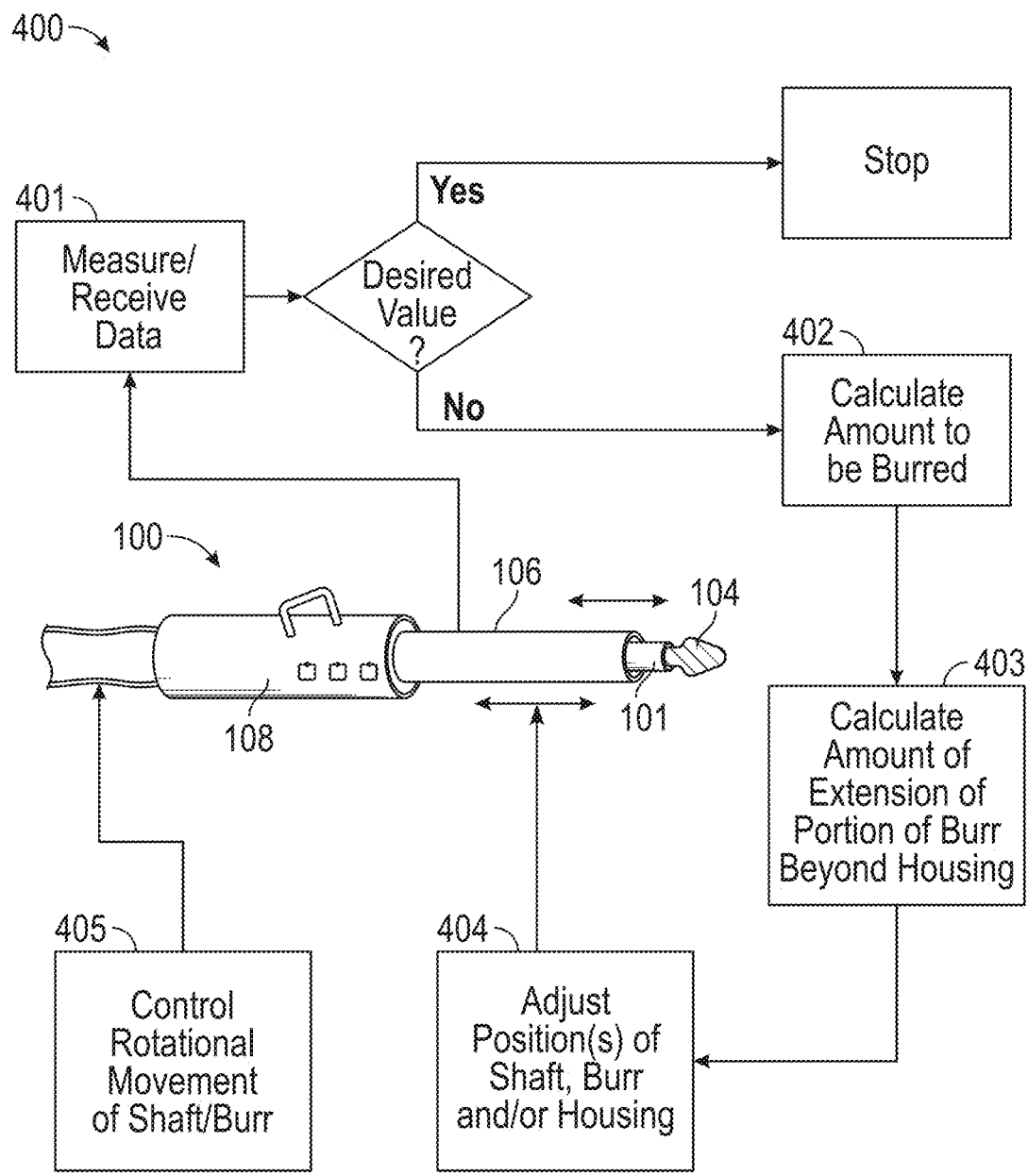
FIG. 5 is a schematic view of a computer-assisted surgical (CAS) system for burring tissue, bone, or cartilage, according to various embodiments.

In another aspect of the disclosure, a computer-assisted surgical (CAS) system 400 may burr tissue, bone, or cartilage. FIG. 5 shows a schematic view of the CAS system 400, according to various embodiments. In some embodiments, the CAS system 400 may include the burring device 100. In some embodiments, the CAS system may include the burr 104 at a distal end 101B of the shaft 101 housed in a housing 106. In some embodiments, one or both of the shaft 101 and housing 106 may be adjustably movable in a linear direction to move the shaft 101 and the housing 106 relative to each other. See, for example, FIG. 3. In some embodiments, the shaft 101 and housing 106 may be adjustably movable in a linear direction relative to each other so that at least a portion of the burr 104 can extend beyond the distal end 106B of the housing 106, as discussed above. See, for example, FIGS. 4B and/or 4C.

In some embodiments, the CAS system 400 may include at least one unit 401 to at least measure data. In some embodiments, the measured data may be related to anatomy of the tissue, bone, or cartilage to be burred. In some embodiments, the measured data may include but not be limited to data related to location, thickness, porosity, and/or density of the tissue, bone, or cartilage to be burred.

In some embodiments, the data measured by the at least one unit 401 may include real-time data related to anatomy of the tissue, bone, or cartilage to be burred. In some embodiments, the real-time data may include but not be limited to data related to thickness, porosity, and/or density of the tissue, bone, or cartilage to be burred.

In some embodiments, the data measured by the at least one unit 401 may include MRI and/or CT imaging data related to anatomy of the tissue, bone, or cartilage to be burred. In some embodiments, the MRI and/or CT imaging data may include real-time data. In some embodiments, the real-time data may include but not be limited to data related to location, thickness, porosity, and/or density of the tissue, bone, or cartilage to be burred.

In some embodiments, the at least one unit 401 may receive data related to anatomy of the tissue, bone, or cartilage to be burred, including but not limited to MRI and/or CT imaging data measured by a separate system (not shown). In some embodiments, the received data may include real-time data measured by the separate system (not shown).

In some embodiments, the at least one unit 401 may compare the measured or received data to predetermined values. In some embodiments, the predetermined data values may include but not be limited to values related to thickness, porosity, and/or density of the tissue, bone, or cartilage to be burred. In some embodiments, the predetermined data values may be input by a user. In some embodiments, the predetermined data values may be values previously stored on the CAS system 400.

In some embodiments, the at least one unit 401 may stop an operation of the CAS system 400 if comparison of the measured or received data to the predetermined data values is within expected value(s) and/or range(s). See, for example, FIG. 5.

In some embodiments, the CAS system 400 may include at least one processor 402 to calculate an amount of tissue, bone, or cartilage to be burred. In some embodiments, the at least one unit 401 of the CAS system 400 may transmit the measured or received data to the at least one processor 402. In some embodiments, the at least one processor 402 may calculate an amount of tissue, bone, or cartilage to be burred based on the data transmitted by the at least one unit 401. In some embodiments, the at least one processor 402 may calculate an amount of tissue, bone, or cartilage to be burred based on predetermined data values. In some embodiments, the predetermined data values may include but not be limited to values related to location, thickness, porosity, and/or density of the tissue, bone, or cartilage to be burred. In some embodiments, the predetermined data values may be input by a user. In some embodiments, the predetermined data values may be values previously stored on the CAS system 400.

In some embodiments, the at least one processor 402 may calculate an amount of tissue, bone, or cartilage to be burred in real-time.

In some embodiments, the CAS system 400 may include at least one processor 403 to calculate an amount of extension y of at least a portion of the burr 104 beyond the distal end 106B of the housing 106. In some embodiments, the at least one processor 402 of the CAS system 400 may transmit the calculated value of the amount of tissue, bone, or cartilage to be burred to the at least one processor 403. In some embodiments, the at least one processor 403 may calculate an amount of extension y based on the calculated value of the amount of tissue, bone, or cartilage to be burred. In some embodiments, the at least one processor 403 may calculate an amount of extension y based on predetermined data values. In some embodiments, at least one equation may include a relationship between an amount of extension y and predetermined data values. In some embodiments, the predetermined data values may include but not be limited to values related to type, location, thickness, porosity, and/or density of the tissue, bone, or cartilage to be burred. In some embodiments, the predetermined data values may be input by a user. In some embodiments, the predetermined data values may be values previously stored on the CAS system 400. In some embodiments, the at least one equation may be previously stored on the CAS system 400.

In some embodiments, the at least one processor 403 may calculate an amount of extension y of at least a portion of the burr 104 beyond the distal end 106B of the housing 106 in real-time.

In some embodiments, the CAS system 400 may include at least one unit 404 to linearly adjust a position of the shaft 101 and/or the burr 104, and a position of the housing 106 relative to each other. In some embodiments, the at least one unit 404 may linearly adjust a position of the shaft 101 and/or the burr 104, and a position of the housing 106 relative to each other so that at least a portion of the burr 104 extends beyond the distal end 106B of the housing 106. In some embodiments, the extension of at least a portion of the burr 104 beyond the distal end 106B of the housing 106 may be substantially equal to the amount of extension y calculated by the at least one processor 403.

In some embodiments, the at least one unit 404 may linearly adjust a position of the shaft 101 and/or the burr 104, and a position of the housing 106 relative to each other in real-time.

In some embodiments, the CAS system 400 may include at least one unit 405 to cause and/or adjust a rotational movement of the burr 104. In some embodiments, the at least one unit 405 may cause and/or adjust a rotational movement of the burr 104 so that the burr 104 burrs an amount of tissue, bone, or cartilage substantially equal to the amount of tissue, bone, or cartilage to be burred calculated by the at least one processor 402.

In some embodiments, the at least one unit 405 may cause and/or adjust a rotational movement of the burr 104 in real-time.

In some embodiments, the CAS system 400 may include at least one memory unit (not shown) to store data. In some embodiments, the stored data may be data measured or received by the at least one unit 401. In some embodiments, the stored data may be data related to the amount of tissue, bone, or cartilage to be burred, calculated by the at least one processor 402. In some embodiments, the stored data may be data related to the amount of extension y of at least a portion of the burr 104 beyond the distal end 106B of the housing 106, calculated by the at least one processor 403. In some embodiments, the stored data may be data related to the position of the shaft 101 and/or the burr 104, and the position of the housing 106, linearly adjusted relative to each other by the at least one unit 404. In some embodiments, the stored data may be data related to the rotational movement of the burr 104, caused and/or adjusted by the at least one unit 405.

In an example operation of an embodiment of the CAS system 400, the operation may include the at least one unit 401 measuring data related to anatomy of the tissue, bone, or cartilage to be burred, including but not limited to real-time MRI and/or CT imaging data related to location, thickness, porosity, and/or density of the tissue, bone, or cartilage. The operation may include the at least one unit 401 comparing the measured data to predetermined values input by a user or previously stored on the CAS system 400. If the at least one unit 401 determines that the measured data is within an expected value and/or range, the at least one unit 401 may stop the operation. If the comparison of the measured data to the predetermined data values is not within an expected value and/or range, the at least one unit 401 may transmit the measured data to the at least one processor 402. The at least one processor 402 may then calculate in real-time an amount of tissue, bone, or cartilage to be burred based on the transmitted data and predetermined data values input by a user or previously stored on the CAS system 400. The at least one processor 402 may then transmit the calculation data of an amount of tissue, bone, or cartilage to be burred to the at least one processor 403. The at least one processor 403 may then calculate in real-time an amount of extension y of at least a portion of the burr 104 beyond the distal end 106B of the housing 106 that may be required to burr the calculated amount of tissue, bone, or cartilage. The at least one processor 403 may calculate the amount of extension y based on predetermined data values input by a user or previously stored on the CAS system 400, and/or an equation relating amount to be burred to amount of extension y. The at least one unit 404 may then linearly adjust in real-time a position of the shaft 101 and/or the burr 104, and a position of the housing 106 of the burring device 100, relative to each other, so that at least a portion of the burr 104 extends beyond the distal end 106B of the housing 106 substantially equal to the calculated amount of extension y. The at least one unit 405 may then cause and/or adjust in real-time a rotational movement of the burr 104 so that the burr 104 burrs an amount of tissue, bone, or cartilage substantially equal to the amount calculated by the at least one processor 402. The operation may be repeated in real-time until the at least one unit 401 stops the operation after determining that the measured data is within an expected value and/or range.

In another aspect of the disclosure, a method for burring tissue, bone, or cartilage may include measuring or receiving data related to anatomy of the tissue, bone, or cartilage. The method may include calculating an amount of tissue, bone, or cartilage to be burred. The amount of tissue, bone or cartilage to be resected may be determined, for example, by a preoperative and/or intraoperative imaging system (not shown) coupled to the burring device 100 and configured to relay the position of the distal end 106B of the housing 106 to the burring device 100. The edge of the distal end 106B of the housing 106 may include a sensor, such as a pressure sensor, (not shown) to detect when the housing 106 makes contact with a bone. Based on data captured by the preoperative and/or intraoperative imaging system (not shown), the burring device 100 may be able to calculate a distance "X" between the position of the distal end 106B of the housing 106 and a target position "T." The burring device 100 may then cause the burr 104 to extend the distance X, burring into the bone until it reaches the target position T. In some embodiments, the distal end 106B of the housing 106 may include a space/feedback sensor rather than a pressure sensor so that the distal end 106B of the housing 106 would not need to contact the bone.

The method may include calculating an amount of extension y of at least a portion of the burr 104 of the burring device 100 beyond the distal end 106B of the housing 106. The housing 106 may house the shaft 101 of the burr 104 and at least a portion of the burr 104. The method may include linearly adjusting a position of the shaft 101 and a position of the housing 106 relative to each other. A position of the shaft 101 and a position of the housing 106 may be linearly adjusted relative to each other so that at least a portion of the burr 104 extends beyond the distal end 106B of the housing 106. The extension of at least a portion of the burr 104 beyond the distal end 106B of the housing 106 may be substantially equal to the calculated amount of extension y. The method may include causing and/or adjusting a rotational movement of the burr 104. The rotational movement of the burr 104 may be such that the burr 104 burrs the calculated amount of tissue, bone, or cartilage.

In some embodiments, at least a portion of the burr 104 extends beyond the distal end 106B of the housing 106 in a range of 1 mm and 15 mm. In some embodiments, the extension y of at least a portion of the burr 104 beyond the distal end 106b of the housing may include an entire length of the burr 104.

In some embodiments, measurement or receipt of the data, calculation of the amount of tissue, bone, or cartilage to be burred, calculation of the amount of extension of at least a portion of the burr 104 beyond the distal end 106B of the housing 106, linear adjustment of the position of the shaft 101 and the position of the housing 106 relative to each other, and/or causation and/or adjustment of the rotational movement of the burr 104 is conducted in real-time.

In some embodiments, the measured or received data may include real-time MRI or CT imaging data of the tissue, bone, or cartilage.

In some embodiments, the method may include storing data related to: the received data, the calculation(s) of the amount(s) to be burred, the calculation(s) of the amount(s) of extension(s), position(s) of the burr relative to the distal end of the housing, and/or the rotational movement(s) of the burr.

Various modifications to the embodiments described in this disclosure will be readily apparent to those skilled in the art, and the generic principles defined herein may be applied to other embodiments without departing from the spirit or scope of this disclosure. Thus, the disclosure is not intended to be limited to the embodiments discussed herein but is to be accorded the widest scope consistent with the claims, the principles and the novel features disclosed herein. The word "example" is used exclusively herein to mean "serving as an example, instance, or illustration." Any embodiment described herein as "example" is not necessarily to be construed as preferred or advantageous over other embodiments, unless otherwise stated.

Certain features that are described in this specification in the context of separate embodiments also may be embodied in combination in a single embodiment. Conversely, various features that are described in the context of a single embodiment also may be embodied in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the order shown or in sequential order, or that all illustrated operations be performed, to achieve desirable results. Additionally, other embodiments are within the scope of the following claims. In some cases, the actions recited in the claims may be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A burring device for burring tissue, bone, or cartilage, the device comprising:
   a shaft comprising a burr attached at a distal end thereof, and configured at a proximal end thereof to be removably attached to a motor configured to drive a rotational movement of the burr; and
   a housing configured to house the shaft in a lengthwise direction and at least a portion of the burr, and configured to allow rotational movement of the burr, and comprising, at a distal portion thereof, an opening through which at least a portion of the burr can extend beyond the housing,
   wherein the shaft is configured to be adjustably movable in a linear direction relative to the housing so that at least a portion of the burr can extend beyond a distal end of the housing by an extension amount, and wherein extension of the at least a portion of the burr beyond the distal end of the housing is controlled by a computer-assisted surgical (CAS) system.

2. The burring device of claim 1, wherein the housing is configured to be adjustably movable in a linear direction relative to the shaft so that at least a portion of the burr can extend beyond a distal end thereof by an extension amount.

3. The burring device of claim 1, wherein the burr is removably attached to the shaft.

4. The burring device of claim 1, wherein the extension amount of the at least a portion of the burr beyond the distal end of the housing is in a range of 1 mm and 15 mm.

5. The burring device of claim 1, wherein the rotational movement of the burr is in a range of 100 rpm and 10,000 rpm.

6. The burring device of claim 1, wherein the extension amount of the at least a portion of the burr beyond the distal end of the housing is controlled by the CAS system in real-time.

7. The burring device of claim 6, wherein the real-time control of the CAS system is based on real-time Magnetic Resonance Imaging (MM) or Computer Tomography (CT) imaging of the tissue, bone, or cartilage anatomy.

8. A CAS system for burring tissue, bone, or cartilage, the system comprising:
- a burring device comprising a burr at a distal end of a shaft housed in a housing, the shaft and housing configured to be adjustably movable in a linear direction relative to each other so that at least a portion of the burr can extend beyond a distal end of the housing;
- at least one unit configured to measure or receive data related to anatomy of the tissue, bone, or cartilage;
- at least one processor configured to calculate an amount of tissue, bone, or cartilage to be burred;
- at least one processor configured to calculate an amount of extension of at least a portion of the burr beyond the distal end of the housing, the amount of extension based on the calculated amount of tissue, bone, or cartilage to be burred;
- at least one unit configured to linearly adjust a position of the shaft and a position of the housing relative to each other so that at least a portion of the burr extends beyond the distal end of the housing, the extension of the burr being substantially equal to the amount of extension calculated by the at least one processor; and
- at least one unit configured to cause and/or adjust a rotational movement of the burr such that the burr burrs an amount of tissue, bone, or cartilage substantially equal to the calculated amount.

9. The CAS system of claim 8, wherein the at least one unit configured to measure or receive data is further configured to compare measured data to predetermined values.

10. The CAS system of claim 8, wherein:
- the measured or received data comprises real-time data,
- the amount of tissue, bone, or cartilage to be burred is calculated in real-time,
- the amount of extension of at least a portion of the burr beyond the distal end of the housing is calculated in real-time,
- the position of the shaft and the position of the housing relative to each other is linearly adjusted in real-time, and
- the rotational movement of the burr is caused and/or adjusted in real-time.

11. The CAS system of claim 10, wherein the measured or received data further comprises MRI or CT imaging data of the tissue, bone, or cartilage.

12. The CAS system of claim 8, wherein the calculation of the amount of tissue, bone, or cartilage to be burred is based on a pre-determined value.

13. The CAS system of claim 8, further comprising at least one memory unit configured to store data related to: the measured or received data, the calculated amount of tissue, bone, or cartilage to be burred, the calculated amount of extension, a position of the burr relative to the distal end of the housing, and/or the rotational movement of the burr.

14. A method for burring tissue, bone, or cartilage, the method comprising:
- measuring or receiving data related to anatomy of the tissue, bone, or cartilage;
- calculating an amount of tissue, bone, or cartilage to be burred;
- calculating an amount of extension of at least a portion of a burr of a burring device beyond a distal end of a housing that houses a shaft of the burr and at least a portion of the burr;
- linearly adjusting a position of the shaft and a position of the housing relative to each other so that at least a portion of the burr extends beyond the distal end of the housing, the extension of the burr substantially equal to the calculated amount of extension; and
- causing and/or adjusting a rotational movement of the burr such that the burr burrs the calculated amount of tissue, bone, or cartilage.

15. The method of claim 14, wherein the at least a portion of the burr extends beyond the distal end of the housing in a range of 1 mm and 15 mm.

16. The method of claim 14, wherein:
- the data related to anatomy is measured or received in real-time,
- the amount of tissue, bone, or cartilage to be burred is calculated in real-time,
- the amount of extension of at least a portion of the burr beyond the distal end of the housing is calculated in real-time,
- the position of the shaft and the position of the housing relative to each other is linearly adjusted in real-time, and/or
- the rotational movement of the burr is caused and/or adjusted in real-time.

17. The method of claim 14, wherein the measured or received data comprises real-time MM or CT imaging data of the tissue, bone, or cartilage.

18. The method of claim 14, wherein the calculation of the amount of tissue, bone, or cartilage to be burred is based on a pre-determined value.

19. The method of claim 14, further comprising storing data related to: the measured or received data, the calculated amount of tissue, bone, or cartilage to be burred, the calculated amount of extension, a position of the burr relative to the distal end of the housing, and/or the rotational movement of the burr.

* * * * *